US00PP20081P2

(12) United States Plant Patent
Lemon

(10) Patent No.: US PP20,081 P2
(45) Date of Patent: Jun. 9, 2009

(54) ***GERANIUM* PLANT NAMED 'OGLGER13067'**

(50) Latin Name: *Pelargonium peltatum*
Varietal Denomination: Oglger13067

(75) Inventor: David Lemon, Lompoc, CA (US)

(73) Assignee: Ecke Geraniums, LLC, Encinitas, CA (US)

( * ) Notice: Subject to any disclaimer, the term of this patent is extended or adjusted under 35 U.S.C. 154(b) by 0 days.

(21) Appl. No.: 12/156,719

(22) Filed: Jun. 3, 2008

(51) Int. Cl.
*A01H 5/00* (2006.01)

(52) U.S. Cl. ..... Plt./332

(58) Field of Classification Search ..... Plt./332
See application file for complete search history.

*Primary Examiner*—Kent L Bell
(74) *Attorney, Agent, or Firm*—C. A. Whealy

(57) ABSTRACT

A new and distinct cultivar of Ivy *Geranium* plant named 'Oglger13067', characterized by its compact, upright to outwardly spreading and mounded plant habit; freely branching habit; freely flowering habit; lavender-colored double flowers; and good garden performance.

1 Drawing Sheet

Botanical designation: *Pelargonium peltatum.*
Cultivar denomination: 'Oglger13067'.

BACKGROUND OF THE INVENTION

The present invention relates to a new and distinct cultivar of Ivy *Geranium,* botanically known as *Pelargonium peltatum,* and hereinafter referred to by the name 'Oglger13067'.

The new Ivy *Geranium* is a product of a planned breeding program conducted by the Inventor in Lompoc, Calif. The objective of the breeding program is to create new compact Ivy *Geranium* cultivars with high temperature tolerance and attractive and unique flower coloration.

The new Ivy *Geranium* originated from a cross-pollination made by the Inventor in February, 2002 in Lompoc, Calif. of a proprietary selection of *Pelargonium peltatum* identified as code number 1683-2, not patented, as the female, or seed, parent with *Pelargonium peltatum* 'Nicole', disclosed in U.S. Plant Pat. No. 7,358, as the male, or pollen, parent. The new Ivy *Geranium* was discovered and selected by the Inventor as a flowering plant from within the progeny of the stated cross-pollination in a controlled greenhouse environment in Connellsville, Pa. in March, 2003.

Asexual reproduction of the new Ivy *Geranium* by vegetative terminal cuttings in a controlled greenhouse environment in Connellsville, Pa. since September, 2003, has shown that the unique features of this new Ivy *Geranium* are stable and reproduced true to type in successive generations.

SUMMARY OF THE INVENTION

The new Ivy *Geranium* has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Oglger13067'. These characteristics in combination distinguish 'Oglger13067' as a new and distinct cultivar of Ivy *Geranium*:

1. Compact, upright to outwardly spreading and mounded plant habit.
2. Freely branching habit.
3. Freely flowering habit.
4. Lavender-colored double flowers.
5. Good garden performance.

Plants of the new Ivy *Geranium* differ from plants of the female parent selection primarily in flower color as plants of the female parent selection have pale lavender-colored flowers. In addition, plants of the new Ivy *Geranium* are more high temperature tolerant than plants of the female parent selection.

Plants of the new Ivy *Geranium* differ from plants of the male parent, 'Nicole', primarily in flower color as plants of 'Nicole' have pink-colored flowers.

Plants of the new Ivy *Geranium* can be compared to plants of *Pelargonium peltatum* 'Freelight Lav Two', disclosed in U.S. Plant Pat. No. 13,230. In side-by-side comparisons conducted in Connellsville, Pa., plants of the new Ivy *Geranium* differed from plants of 'Freelight Lav Two' in the following characteristics:

1. Plants of the new Ivy *Geranium* were more compact than plants of 'Freelight Lav Two'.
2. Plants of the new Ivy *Geranium* flowered earlier than plants of 'Freelight Lav Two'.

BRIEF DESCRIPTION OF THE PHOTOGRAPHS

The accompanying colored photographs illustrate the overall appearance of the new Ivy *Geranium*, showing the colors as true as it is reasonably possible to obtain in colored reproductions of this type. Colors in the photographs may differ slightly from the color values cited in the detailed botanical description which accurately describe the colors of the new Ivy *Geranium*.

The photograph at the bottom of the sheet comprises a side perspective view of a typical flowering plant of 'Oglger13067' grown in a container.

The photograph at the top of the sheet is a close-up view of typical flowers of 'Oglger13067'.

DETAILED BOTANICAL DESCRIPTION

The aforementioned photographs and following observations, measurements and values describe plants grown in Encinitas, Calif. in a plastic-covered greenhouse during the spring and under conditions which closely approximate Ivy *Geranium* commercial production. During the production of the plants, day temperatures averaged 24° C., night temperatures averaged 19° C. and light levels averaged 4,000 foot-candles. Plants were about 15 weeks from planting when the photographs and the description were taken. In the detailed description, color references are made to The Royal Horticultural Society Colour Chart, 1995 Edition, except where general terms of ordinary dictionary significance are used.

Botanical classification: *Pelargonium peltatum* 'Oglger13067'.

Parentage:

*Female, or seed, parent.*—Proprietary selection of *Pelargonium peltatum* identified as code number 1683-2, not patented.

*Male or pollen parent.*—*Pelargonium peltatum* 'Nicole', disclosed in U.S. Plant Pat. No. 7,358.

Propagation:

*Type.*—By vegetative terminal cuttings.

*Time to initiate roots, summer.*—About ten days at temperatures of 20° C.

*Time to initiate roots, winter.*—About two weeks at temperatures of 16° C.

*Time to produce a rooted young plant, summer.*—About four weeks at temperatures of 20° C.

*Time to produce a rooted young plant, winter.*—About four weeks at temperatures of 16° C.

*Root description.*—Fine, fibrous; white in color.

*Rooting habit.*—Freely branching.

Plant description:

*General appearance.*—Compact, upright to somewhat outwardly spreading plant habit; uniformly mounded; densely foliated.

*Growth and branching habit.*—Moderately vigorous to vigorous growth habit. Freely branching habit; about six primary lateral branches develop per plant.

*Plant height, to top of foliar plane.*—About 11 cm.

*Plant height, to top of umbels.*—About 21.5 cm.

*Plant diameter (spread).*—About 19 cm by 24 cm.

*Lateral branches.*—Length: About 9.8 cm. Diameter: About 4 mm. Internode length: About 1.4 cm. Texture: Pubescent. Strength: Strong. Color: Close to 146B.

Foliage description:

*Arrangement.*—Initially opposite, becoming alternate when flowers develop; simple.

*Length.*—About 6.5 cm.

*Width.*—About 6.3 cm.

*Shape.*—Nearly rounded with five shallow lobes.

*Apex.*—Broadly acute to rounded.

*Base.*—Cordate; slightly imbricate.

*Margin.*—Entire with five shallow lobes.

*Venation pattern.*—Palmate.

*Texture, upper and lower surfaces.*—Pubescent; slightly coarse.

*Color.*—Developing foliage, upper surface: Close to 146A. Developing foliage, lower surface: Close to 146B. Fully expanded foliage, upper surface: Close to 147A; venation, close to 146B. Fully expanded foliage, lower surface: Close to 147B; venation, close to 146C. Zonation pattern: Not observed.

*Petiole.*—Length: About 6.2 cm. Diameter: About 2 mm. Texture, upper and lower surfaces: Smooth, glabrous. Color, upper and lower surfaces: Close to 146B.

Flower description:

*Flower arrangement.*—Rotate double flowers arranged in rounded almost hemispherical umbels arising from apical leaf axils. Umbels displayed above the foliage on strong peduncles. Flowers face upright to outward; flowers slightly cupped becoming flatter with development.

*Fragrance.*—None detected.

*Quantity of flowers.*—Freely flowering habit; about five flowers per umbel; about five to six umbels per plant at one time.

*Flowering season.*—In Encinitas, Calif., flowering is continuous during the spring and summer.

*Flower longevity.*—Individual flowers last about three to four days on the plant; flowers persistent.

*Umbel height.*—About 4.4 cm.

*Umbel diameter.*—About 7 cm.

*Flower diameter.*—About 3.8 cm.

*Flower depth (height).*—About 2 cm.

*Flower buds.*—Length: About 2 cm. Diameter: About 9 mm. Shape: Elliptical. Color: Close to 157A.

*Petals.*—Quantity per flower: About eleven to twelve in two whorls. Length: About 2 cm to 2.5 cm. Width: About 8 mm to 9 mm. Shape: Roughly obovate. Apex: Rounded. Base: Attenuate. Margin: Entire. Texture, upper and lower surfaces: Smooth, glabrous; velvety. Color: When opening, upper surface: Close to 84B. When opening, lower surface: Close to 76D. Fully opened, upper three petals, upper surface: Close to 84B; towards the base, longitudinal stripes, close to 61A; at the base, close to 58A; venation, close to 58A. Color becoming closer to 76B with development. Fully opened, lower two petals, upper surface: Close to 84B; at the base, close to 75D; venation, close to 84B. Color becoming closer to 76B with development. Fully opened, upper three petals, lower surface: Close to 76D; at the base, close to 60D; venation, close to 60D. Fully opened, lower two petals, lower surface: Close to 76D; at the base, close to 76D; venation, close to 76D.

*Petaloids.*—Quantity per flower: About two or three. Length: About 1.4 cm. Width: About 3 mm. Shape: Irregular, mostly oblong. Apex: Rounded. Base: Attenuate. Margin: Entire. Texture, upper and lower surfaces: Smooth, glabrous; velvety. Color: When opening, upper surface: Close to 84B. When opening, lower surface: Close to 77D. Fully opened, upper surface: Close to 75C; at the base, close to 75D; venation, close to 75C. Color becoming closer to 84C with development. Fully opened, lower surface: Close to 76D; at the base, close to 75D; venation, close to 75D.

*Sepals.*—Quantity per flower: Five, arranged in a single whorl. Length: About 1.2 cm. Width: About 3.5 mm. Shape: Lanceolate. Apex: Acuminate. Base: Attenuate. Margin: Entire. Texture, upper surface: Smooth, glabrous. Texture, lower surface: Pubescent. Color, upper and lower surfaces: Close to 146B.

*Peduncle (umbel stem).*—Length: About 10.5 cm. Diameter: About 2.5 mm. Strength: Strong. Texture: Pubescent. Color: Close to 146C.

*Pedicel* (*individual flower stem*).—Length: About 2.7 cm. Diameter: About 1.5 mm. Strength: Strong. Texture: Pubescent. Color: Close to 146B.

*Reproductive organs.*—Androecium: Stamen quantity per flower: About five. Anther size: About 1 mm by 2 mm. Anther shape: Oblong. Anther color: Close to 79D. Pollen amount: Scarce. Pollen color: Close to 164A. Gynoecium: Pistil quantity per flower: One. Pistil length: About 9 mm. Stigma shape: Split into five parts. Stigma color: Close to 59A. Style length: About 2 mm. Style color: Close to 186D. Ovary color: Close to 148D.

*Seed/fruit.*—Seed and fruit development have not been observed.

Disease/pest resistance: Plants of the new Ivy *Geranium* have not been observed to be resistant to pathogens and pests common to Ivy *Geraniums*.

Garden performance: Plants of the new Ivy *Geranium* have been observed to tolerate rain, wind, and temperatures ranging from about 4° C. to about 35° C. and have demonstrated good garden performance.

It is claimed:

1. A new and distinct Ivy *Geranium* plant named 'Oglger13067' as illustrated and described.

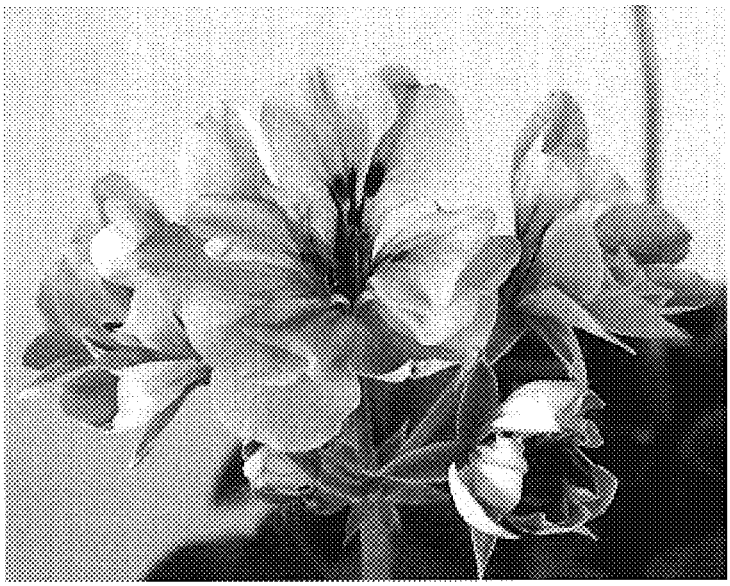
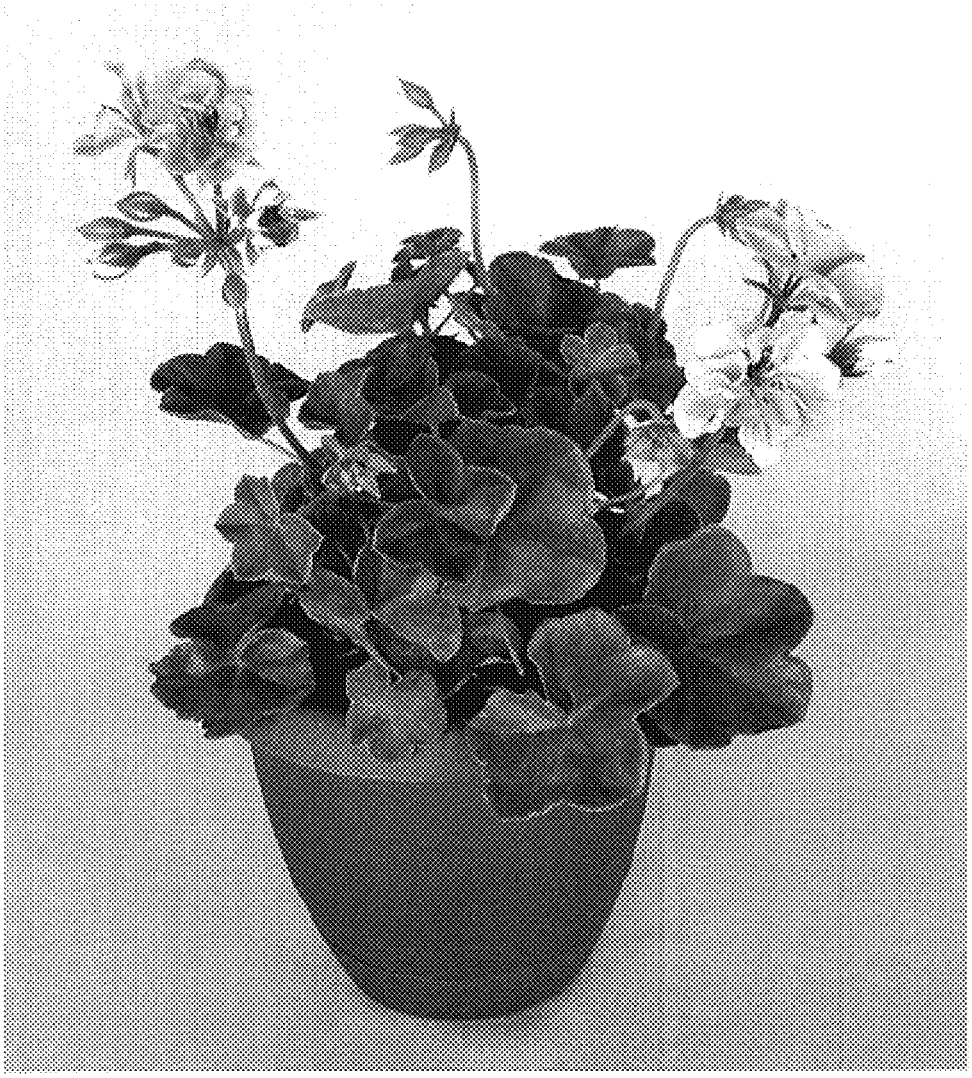

* * * * *